United States Patent [19]
Gough et al.

[11] Patent Number: 5,863,290
[45] Date of Patent: *Jan. 26, 1999

[54] MULTIPLE ANTENNA ABLATION APPARATUS AND METHOD

[75] Inventors: Edward J. Gough, Menlo Park; Alan A. Stein, Moss Beach, both of Calif.

[73] Assignee: Rita Medical Systems, Mountain View, Calif.

[ * ] Notice: The term of this patent shall not extend beyond the expiration date of Pat. No. 5,683,384.

[21] Appl. No.: 574,618

[22] Filed: Dec. 19, 1995

Related U.S. Application Data

[63] Continuation-in-part of Ser. No. 515,379, Aug. 15, 1995, Pat. No. 5,683,384.

[51] Int. Cl.$^6$ .................................................. A61B 17/36
[52] U.S. Cl. .............................. 606/41; 606/42; 607/101; 607/105
[58] Field of Search ........................... 606/41, 42, 45–50; 607/100–102, 104, 105

[56] References Cited

U.S. PATENT DOCUMENTS

| | | |
|---|---|---|
| Re. 32,057 | 12/1985 | Leveen . |
| Re. 32,066 | 1/1986 | Leveen . |
| 3,991,770 | 11/1976 | Leveen . |
| 4,016,886 | 4/1977 | Doss . |
| 4,043,342 | 8/1977 | Morrison, Jr. . |
| 4,074,718 | 2/1978 | Morrison, Jr. . |
| 4,080,959 | 3/1978 | Leveen . |
| 4,095,602 | 6/1978 | Leveen . |
| 4,119,102 | 10/1978 | Leveen . |
| 4,140,130 | 2/1979 | Storm, III . |
| 4,154,246 | 5/1979 | Leveen . |
| 4,230,129 | 10/1980 | Leveen . |
| 4,285,346 | 8/1981 | Armitage . |
| 4,290,435 | 9/1981 | Waggott . |
| 4,303,636 | 12/1981 | Gordon . |
| 4,346,715 | 8/1982 | Cammell . |
| 4,375,220 | 3/1983 | Matvias . |
| 4,545,368 | 10/1985 | Rand et al. . |
| 4,565,200 | 1/1986 | Cosman . |
| 4,574,782 | 3/1986 | Borrelli . |
| 4,586,490 | 5/1986 | Katz . |
| 4,676,258 | 6/1987 | Inokuchi et al. . |
| 4,709,701 | 12/1987 | Weber . |
| 4,763,671 | 8/1988 | Goffinet . |
| 4,800,899 | 1/1989 | Elliott . |
| 4,813,429 | 3/1989 | Eshel . |
| 4,823,791 | 4/1989 | D'Amelio . |
| 4,860,744 | 8/1989 | Johnson . |
| 4,881,543 | 11/1989 | Trembly et al. . |
| 4,887,614 | 12/1989 | Shirakami et al. . |
| 4,920,978 | 5/1990 | Colvin . |
| 4,931,047 | 6/1990 | Broadwin . |
| 4,945,912 | 8/1990 | Langberg . |
| 4,947,842 | 8/1990 | Marchosky . |
| 4,962,761 | 10/1990 | Golden . |
| 4,976,680 | 12/1990 | Hayman . |
| 4,976,711 | 12/1990 | Parins . |
| 4,983,159 | 1/1991 | Rand . |
| 5,003,991 | 4/1991 | Takayama et al. . |
| 5,007,908 | 4/1991 | Rydell . |
| 5,009,656 | 4/1991 | Reimels . |

(List continued on next page.)

FOREIGN PATENT DOCUMENTS

| | | |
|---|---|---|
| 2124684 | 11/1972 | Germany . |
| WO 96/29946 | 10/1996 | WIPO . |

*Primary Examiner*—Michael Peffley
*Attorney, Agent, or Firm*—Wilson Sonsini Goodrich & Rosati

[57] ABSTRACT

An ablation treatment apparatus includes an energy source. A multiple antenna device is included and has a primary antenna with a longitudinal axis, a central lumen and a distal end, and a secondary antenna with a distal end. The secondary antenna is deployed from the primary antenna central lumen in a lateral direction to the longitudinal axis. A selected primary or secondary antenna is electromagnetically coupled to the energy source. A non-selected antenna is electromagnetically coupled to the selected antenna. A cable connects the energy source to the selected antenna.

43 Claims, 8 Drawing Sheets

U.S. PATENT DOCUMENTS

| | | |
|---|---|---|
| 5,010,897 | 4/1991 | Leveen . |
| 5,047,027 | 9/1991 | Rydell . |
| 5,057,107 | 10/1991 | Parins . |
| 5,067,952 | 11/1991 | Gudov . |
| 5,071,419 | 12/1991 | Rydel . |
| 5,078,717 | 1/1992 | Parins . |
| 5,085,649 | 2/1992 | Rydell . |
| 5,099,756 | 3/1992 | Franconi . |
| 5,100,423 | 3/1992 | Fearnot . |
| 5,122,137 | 6/1992 | Lennox . |
| 5,125,928 | 6/1992 | Parins . |
| 5,190,517 | 3/1993 | Zieve et al. . |
| 5,190,541 | 3/1993 | Abele . |
| 5,197,466 | 3/1993 | Marchosky . |
| 5,197,963 | 3/1993 | Parins . |
| 5,197,964 | 3/1993 | Parins . |
| 5,203,782 | 4/1993 | Gudov . |
| 5,217,458 | 6/1993 | Parins . |
| 5,236,410 | 8/1993 | Granov . |
| 5,246,438 | 9/1993 | Langberg . |
| 5,257,451 | 11/1993 | Edwards . |
| 5,273,535 | 12/1993 | Edwards . |
| 5,275,162 | 1/1994 | Edwards . |
| 5,277,696 | 1/1994 | Hagen . |
| 5,281,217 | 1/1994 | Edwards . |
| 5,281,218 | 1/1994 | Imran . |
| 5,282,797 | 2/1994 | Chess . |
| 5,290,286 | 3/1994 | Parins . |
| 5,293,869 | 3/1994 | Edwards . |
| 5,295,955 | 3/1994 | Rosen . |
| 5,309,910 | 5/1994 | Edwards . |
| 5,313,943 | 5/1994 | Houser . |
| 5,314,466 | 5/1994 | Stern . |
| 5,328,467 | 7/1994 | Edwards . |
| 5,334,193 | 8/1994 | Nardella . |
| 5,342,357 | 8/1994 | Nardella . |
| 5,348,554 | 9/1994 | Imran et al. . |
| 5,363,861 | 11/1994 | Edwards . |
| 5,366,490 | 11/1994 | Edwards . |
| 5,368,592 | 11/1994 | Stern . |
| 5,370,675 | 12/1994 | Edwards . |
| 5,370,678 | 12/1994 | Edwards . |
| 5,383,917 | 1/1995 | Desai ..................................... 607/702 |
| 5,385,544 | 1/1995 | Edwards et al. . |
| 5,398,683 | 3/1995 | Edwards . |
| 5,409,453 | 4/1995 | Lundquist . |
| 5,421,819 | 6/1995 | Edwards . |
| 5,423,708 | 6/1995 | Edwards . |
| 5,423,807 | 6/1995 | Milder . |
| 5,423,811 | 6/1995 | Imran et al. . |
| 5,433,708 | 7/1995 | Nichols . |
| 5,435,805 | 7/1995 | Edwards . |
| 5,437,662 | 8/1995 | Nardella . |
| 5,456,662 | 10/1995 | Edwards . |
| 5,456,682 | 10/1995 | Edwards . |
| 5,458,596 | 10/1995 | Lax . |
| 5,458,597 | 10/1995 | Edwards . |
| 5,462,521 | 10/1995 | Bruckner et al. . |
| 5,470,308 | 11/1995 | Edwards . |
| 5,470,309 | 11/1995 | Edwards . |
| 5,471,982 | 12/1995 | Edwards . |
| 5,472,441 | 12/1995 | Edwards . |
| 5,484,400 | 1/1996 | Edwards . |
| 5,486,161 | 1/1996 | Lax . |
| 5,505,730 | 4/1996 | Edwards . |
| 5,507,743 | 4/1996 | Edwards et al. . |
| 5,509,419 | 4/1996 | Edwards . |
| 5,514,130 | 5/1996 | Baker . |
| 5,514,131 | 5/1996 | Edwards . |
| 5,531,676 | 7/1996 | Edwards . |
| 5,531,677 | 7/1996 | Lundquist et al. . |
| 5,536,240 | 7/1996 | Edwards . |
| 5,536,267 | 7/1996 | Edwards et al. . |
| 5,540,655 | 7/1996 | Edwards . |
| 5,542,915 | 8/1996 | Edwards . |
| 5,542,916 | 8/1996 | Hirsch . |
| 5,542,928 | 8/1996 | Evans . |
| 5,545,161 | 8/1996 | Imran . |
| 5,545,171 | 8/1996 | Sharkey . |
| 5,545,193 | 8/1996 | Fleischman . |
| 5,546,267 | 8/1996 | Frederiksen . |
| 5,549,108 | 8/1996 | Edwards . |
| 5,549,644 | 8/1996 | Lundquist . |
| 5,554,110 | 9/1996 | Edwards . |
| 5,556,377 | 9/1996 | Rosen . |
| 5,558,672 | 9/1996 | Edwards . |
| 5,558,673 | 9/1996 | Edwards . |
| 5,560,358 | 10/1996 | Arnold et al. . |
| 5,562,703 | 10/1996 | Desai . |

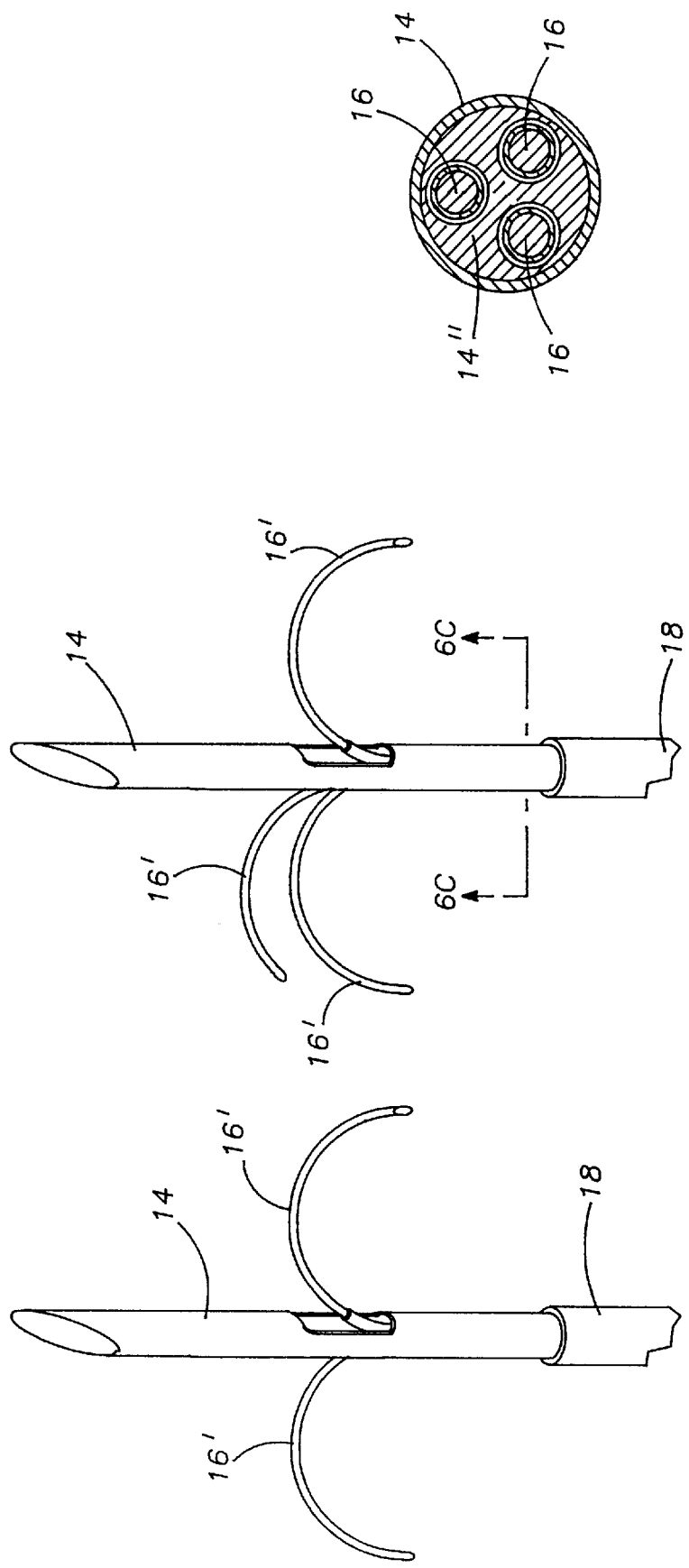

MULTIPLE ANTENNA ABLATION APPARATUS AND METHOD

REFERENCE TO RELATED APPLICATION

This application is a continuation-in-part of U.S. patent application Ser. No. 08/515,379, filed Aug. 15, 1995, now U.S. Pat. No. 5,683,384 entitled "Multiple Antenna Ablation Apparatus", incorporated herein by reference.

BACKGROUND OF THE INVENTION

1. Field of the Invention

This invention relates generally to an RF treatment and ablation apparatus that includes a primary antenna inserted into or adjacent to a selected body mass, such as a tumor, with one or more side deployed secondary antennas that are electromagnetically coupled to the primary antenna, and more particularly to a multiple antenna RF treatment and ablation apparatus with one or more secondary antennas electromagnetically coupled to the primary antenna.

2. Description of the Related Art

Current open procedures for treatment of tumors are extremely disruptive and cause a great deal of damage to healthy tissue. During the surgical procedure, the physician must exercise care in not cutting the tumor in a manner that creates seeding of the tumor, resulting in metastasis. In recent years, development of products has been directed with an emphasis on minimizing the traumatic nature of traditional surgical procedures.

There has been a relatively significant amount of activity in the area of hyperthermia as a tool for treatment of tumors. It is known that elevating the temperature of tumors is helpful in the treatment and management of cancerous tissues. The mechanisms of selective treatment are not completely understood. However, four cellular effects of hyperthermia on cancerous tissue have been proposed, (i) changes in cell or nuclear membrane permeability or fluidity, (ii) cytoplasmic lysomal disintegration, causing release of digestive enzymes, (iii) protein thermal damage affecting cell respiration and the synthesis of DNA or RNA and (iv) potential excitation of immunologic systems. Treatment methods for applying heat to tumors include the use of direct contact radio-frequency (RF) applicators, microwave radiation, inductively coupled RF fields, ultrasound, and a variety of simple thermal conduction techniques.

Among the problems associated with all of these procedures is the requirement that highly localized heat be produced at depths of several centimeters beneath the surface of the skin. RF applications may be used at depth during surgery. However, the extent of localization is generally poor, with the result that healthy tissue may be harmed.

With RF lesion making, a high frequency alternating current flows from the electrode into the tissue. Ionic agitation is produced in the region of tissue about the electrode tip as the ions attempt to follow the directional variations of the alternating current. This agitation results in frictional heating so that the tissue about the electrode, rather than the electrode itself, is the primary source of heat. Tissue heat generated is produced by the flow of current through the electrical resistance offered by the tissue. The greater this resistance, the greater the heat generated.

Lesion size ultimately is governed by tissue temperature. Some idea of tissue temperature can be obtained by monitoring the temperature at an electrode or probe tip, usually with a thermistor. RF lesion heat is generated within the tissue, the temperature monitored will be the resultant heating of the electrode by the lesion. RF lesion heat is generated within the tissue, the temperature monitored is the resultant heating of the probe by the lesion. A temperature gradient extends from the lesion to the probe tip, so that the probe tip is slightly cooler than the tissue immediately surrounding it, but substantially hotter than the periphery of the lesion because of the rapid attenuation of heating effect with distance.

Current spreads out radially from the electrode tip, so that current density is greatest next to the tip, and decreases progressively at distances from it. The frictional heat produced from ionic agitation is proportional to current, i.e., ionic density. Therefore, the heating effect is greatest next to the electrode and decreases with distance from it. One consequence of this is that lesions can inadvertently be made smaller than anticipated for a given electrode size if the RF current level is too high. There must be time for equilibrium heating of tissue to be reached, especially at center the of the desired lesion volume. If the current density is too high, the tissue temperature next to the electrode rapidly exceeds desired levels and carbonization and boiling occurs in a thin tissue shell surrounding the electrode tip.

There is a need for a multiple antenna ablation apparatus, defined by a primary antenna and secondary antennas that are electromagnetically coupled to the primary antenna, with sensors positioned at distal ends of each antenna, and the primary antenna is electromagnetically coupled to an energy source.

SUMMARY OF THE INVENTION

Accordingly, an object of the invention is to provide an ablation apparatus with a primary arm that is introduced into a selected solid mass and secondary arms that are deployed laterally from the primary arm, and the secondary arms are electromagnetically coupled to the primary antenna to receive energy from the primary antenna.

A further object of the invention is to provide an ablation apparatus with one or more secondary antennas electromagnetically coupled to a primary antenna, and the primary antenna is electromagnetically coupled to an energy source.

Yet another object of the invention is to provide an ablation apparatus that is introduced into a selected mass, defines the periphery of a selected ablation volume during the ablation process, and achieves the ablation with RF energy, microwave energy, laser energy, or any combination thereof.

A further object of the invention is to provide a multiple antenna ablation apparatus that includes an ability to introduce a variety of infusion mediums.

These and other objectives are achieved in an ablation treatment apparatus. The apparatus includes an energy source producing an ablation energy output. A multiple antenna device is included and has a primary antenna with a longitudinal axis, a central lumen and a distal end, and a secondary antenna with a distal end. The secondary antenna is deployed from the primary antenna central lumen in a lateral direction to the longitudinal axis. A selected primary or secondary antenna is electromagnetically coupled to the energy source. A non-selected antenna is electromagnetically coupled to the selected antenna. A cable connects the energy source to the selected antenna.

In another embodiment, a method is disclosed for ablating a selected tissue mass. The method provides an ablation device with an energy source, a primary antenna, and a secondary antennas housed in a primary antenna lumen formed in the primary antenna. One of the primary or secondary antennas is selected and electromagnetically coupled to the energy source. The non-selected antenna is coupled to the selected antenna. A cable couples the selected antenna to the energy source. The primary antenna is inserted into the selected tissue mass with the secondary antenna positioned in the primary antenna lumen. A distal end of the secondary antenna is advanced into the selected tissue mass from the primary antenna lumen in a lateral direction relative to a longitudinal axis of the primary antenna. Electromagnetic energy is delivered from one of a primary antenna ablation surface, a secondary antenna ablation surface or both to the selected tissue mass. An ablation volume is created in the selected tissue mass.

The multiple antenna device can be an RF antenna, a microwave antenna, a short wave antenna and the like. At least two secondary antennas can be included and be laterally deployed from the primary antenna. The secondary antenna is retractable into the primary antenna, permitting repositioning of the primary antenna. When the multiple antenna is an RF antenna, it can be operated in mono-polar or bipolar modes, and is capable of switching between the two.

Further, the multiple antenna device can be a multi-modality apparatus. One or all of the antennas can be hollow to receive an infusion medium from an infusion source and introduce the infusion medium into a selected tissue mass. A multiplexer can be coupled to the primary antenna, secondary antenna and power supply to effect multiplexing between the primary and secondary antennas.

An insulation sleeve can be positioned around the primary and secondary antennas. Another sensor is positioned at the distal end of the insulation sleeve surrounding the primary antenna.

BRIEF DESCRIPTION OF THE FIGURES

FIG. 6(*a*) is a perspective view of the multiple antenna ablation of the present invention illustrating two secondary antennas which provide a retaining and gripping function.

FIG. 6(*b*) is a perspective view of the multiple antenna ablation of the present invention illustrating three secondary antennas which provide a retaining and gripping function.

FIG. 6(*c*) is a cross-sectional view of the apparatus of FIG. 6(*b*) taken along the lines 6(*c*)—6(*c*).

DETAILED DESCRIPTION

Figure 1:
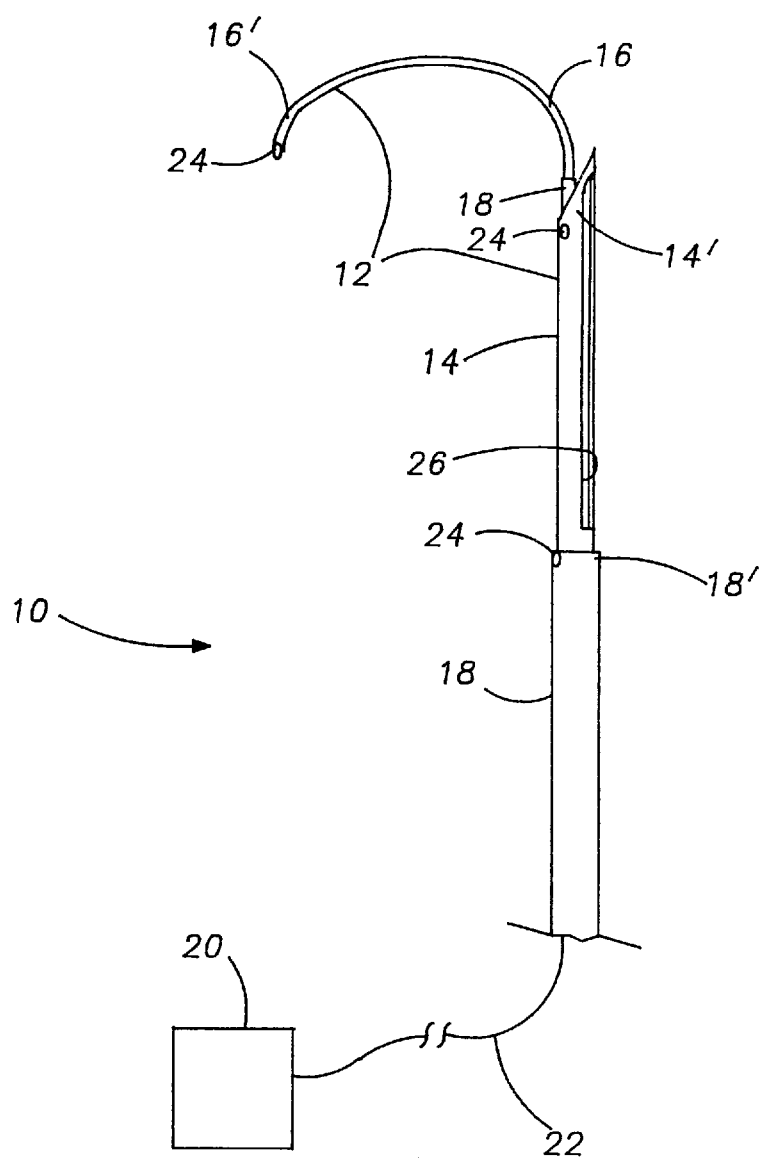
FIG. 1 is a perspective view of the multiple antenna ablation apparatus of the present invention illustrating a primary antenna and a single laterally deployed secondary antenna.

As shown in FIG. 1, an ablation treatment apparatus 10 includes a multiple antenna device 12. Multiple antenna device 12 includes a primary antenna 14, and one or more secondary antennas 16, which are typically electrodes. Secondary antennas 16 are initially positioned in a primary antenna lumen when primary antenna 14 is advanced through tissue. When primary antenna 14 reaches a selected tissue ablation site in a selected tissue mass, including but not limited to a solid lesion, secondary antennas 16 are laterally deployed from the primary antenna lumen and into the selected tissue mass. Ablation proceeds from the interior of the selected tissue mass in a direction towards a periphery of the selected tissue mass.

Each primary and secondary antenna 14 and 16 has an exterior ablation surface which delivers electromagnetic energy to the selected tissue mass. The length and size of each ablation surface can be variable. The length of primary antenna ablation surface relative to secondary antenna ablation surface can be 20% or greater, 33 and ⅓% or greater, 50% or greater, 75% or greater, about the same length, or greater than the length of secondary electrode ablation surface. Lengths of primary and secondary antennas 14 and 16 can be adjustable. Primary antenna 14 can be moved up and down, rotated about its longitudinal axis, and moved back and forth, in order to define, along with sensors, the periphery or boundary of the selected tissue mass, including but not limited to a tumor. This provides a variety of different geometries, not always symmetrical, that can be ablated. The ablation can be between the ablation surfaces of primary and secondary antennas 14 and 16 when operated in a monopolar mode with a ground pad.

Primary antenna 14 is constructed so that it can be introduced percutaneously or laparoscopically through tissue without an introducer. Primary antenna 14 combines the function of an introducer and an electrode. Primary antenna 14 can have a sharpened distal end 14' to assist introduction through tissue. Each secondary antenna 16 has a distal end 16' that is constructed to be less structurally rigid than primary antenna 14. Distal end 16' is that section of secondary antenna 16 that is advanced from the lumen antenna 14 and into the selected tissue mass. Distal end is typically less structurally rigid that primary antenna 14. However, even though sections of secondary antenna 16 which are not advanced through the selected tissue mass may be less structurally rigid than primary antenna 14.

Structurally rigidity is determined by, (i) choosing different materials for antenna 14 and and distal end 16' or some greater length of secondary antenna 16, (ii) using the same material but having less of it for secondary antenna 16 or distal end 16', e.g., secondary antenna 16 or distal end 16' is not as thick as primary electrode 14, or (iii) including another material in one of the antennas 14 or 16 to vary their structural rigidity. For purposes of this disclosure, structural rigidity is defined as the amount of deflection that an antenna has relative to its longitudinal axis. It will be appreciated that a given antenna will have different levels of rigidity depending on its length.

Primary and secondary antennas 14 and 16 can be made of a variety of conductive materials, both metallic and non-metallic. One suitable material is type 304 stainless steel of hypodermic quality. In some applications, all or a portion of secondary electrode 16 can be made of a shaped memory metal, such as NiTi, commercially available from Raychem Corporation, Menlo Park, Calif.

Each of primary or secondary antennas 14 or 16 can have different lengths. The lengths can be determined by the actual physical length of an antenna, the amount of an antenna that has an ablation delivery surface, and the length of an antenna that is not covered by an insulator. Suitable lengths include but are not limited to 17.5 cm, 25.0 cm. and 30.0 cm. The actual length of an antenna depends on the location of the selected tissue mass to be ablated, its distance from the skin, its accessibility as well as whether or not the physician chooses a laproscopic, percutaneous or other procedure. Further, ablation treatment apparatus 10, and more particularly multiple antenna device 12, can be introduced through a guide to the desired tissue mass site.

An insulation sleeve 18 may be positioned around an exterior of one or both of the primary and secondary antennas 14 and 16 respectively. Preferably, each insulation sleeve 18 is adjustably positioned so that the length of an antenna ablation surface can be varied. Each insulation sleeve 18 surrounding a primary antenna 14 can include one or more apertures. This permits the introduction of a secondary antenna 16 through primary antenna 14 and insulation sleeve 18.

In one embodiment, insulation sleeve 18 can comprise a polyamide material. A sensor 24 may be positioned on top of polyimide insulation sleeve 18. The polyamide insulation sleeve 18 is semi-rigid. Sensor 24 can lay down substantially along the entire length of polyamide insulation sleeve 18. Primary antenna 14 is made of a stainless-steel hypodermic tubing with 2 cm of exposed ablation surface. Secondary antennas 16 have distal ends 16' that are made of NiTi hypodermic tubing. A handle is included with markings to show the varying distance of secondary antennas 16 from primary antenna 14. Fluid infusion is delivered through a Luer port at a side of the handle. Type-T thermocouples are positioned at distal ends 16'.

An energy source 20 is connected to multiple antenna device 12 with one or more cables 22. Energy source 20 can be an RF source, microwave source, short wave source, laser source and the like. Multiple antenna device 12 can be comprised of primary and secondary antennas 14 and 16 that are RF electrodes, microwave antennas, as well as combinations thereof. Energy source 20 may be a combination RF/microwave box. Further a laser optical fiber, coupled to a laser source 20 can be introduced through one or both of primary or secondary antennas 14 and 16. One or more of the primary or secondary antennas 14 and 16 can be an arm for the purposes of introducing the optical fiber.

Antennas 14 and 16 may be electromagnetically coupled by wiring, soldering, connection to a common couplet, and the like. This permits only one antenna 14 or 16 to be coupled to energy source 20 and use of a single cable 22.

One or more sensors 24 may be positioned on interior or exterior surfaces of primary antenna 14, secondary antenna 16 or insulation sleeve 18. Preferably sensors 24 are positioned at primary antenna distal end 14', secondary antenna distal end 16' and insulation sleeve distal end 18'. Sensors 24 permit accurate measurement of temperature at a tissue site in order to determine, (i) the extent of ablation, (ii) the amount of ablation, (iii) whether or not further ablation is needed and (iv) the boundary or periphery of the ablated mass. Further, sensors 24 prevent non-targeted tissue from being destroyed or ablated.

Sensors 24 are of conventional design, including but not limited to thermistors, thermocouples, resistive wires, and the like. Suitable thermal sensors 24 include a T type thermocouple with copper constantene, J type, E type, K type, fiber optics, resistive wires, thermocouple IR detectors, and the like. It will be appreciated that sensors 24 need not be thermal sensors.

Sensors 24 measure temperature and/or impedance to permit monitoring and a desired level of ablation to be achieved without destroying too much tissue. This reduces damage to tissue surrounding the targeted mass to be ablated. By monitoring the temperature at various points within the interior of the selected tissue mass, a determination of the selected tissue mass periphery can be made, as well as a determination of when ablation is complete. If at any time sensor 24 determines that a desired ablation temperature is exceeded, then an appropriate feedback signal is received at energy source 20 which then regulates the amount of energy delivered to primary and/or secondary antennas 14 and 16.

Thus the geometry of the ablated mass is selectable and controllable. Any number of different ablation geometries can be achieved. This is a result of having variable lengths for primary antenna 14 and secondary antenna 16 ablation surfaces as well as the inclusion of sensors 24.

Preferably, distal end 16' is laterally deployed relative to a longitudinal axis of primary antenna 14 out of an aperture 26 formed in primary antenna 14. Aperture 26 is at distal end 14' or formed in a side of an exterior of antenna 14.

A method for creating an ablation volume in a selected tissue mass includes inserting and advancing primary antenna 14 through tissue and into a selected tissue mass. Secondary antennas 16 are positioned in a lumen formed in antenna 14 while antenna 14 is advanced through tissue. At least one distal end 16' is deployed from the primary antenna lumen into the selected tissue mass in a lateral direction relative to the longitudinal axis of primary antenna 14. Electromagnetic energy is delivered from one of a primary antenna ablation surface, a secondary antenna ablation surface or both to the selected tissue mass.

An ablation volume is created in the selected tissue mass. When operated in the monopolar mode, the ablation is between the ablation surfaces of the antennas.

There is wide variation in the amount of deflection of secondary antenna 16. For example, secondary antenna 16 can be deflected a few degrees from the longitudinal axis of primary antenna 14, or secondary antenna can be deflected in any number of geometric configurations, including but not limited to a "J" hook. Further, secondary antenna 16 is capable of being introduced from primary antenna 14 a few millimeters from primary antenna 14, or a much larger distance. Ablation by secondary antenna 16 can begin a few millimeters away from primary antenna 14, or secondary electrode 16 can be advanced a greater distance from primary antenna 14 and at that point the initial ablation by secondary antenna 16 begins.

Figure 2:
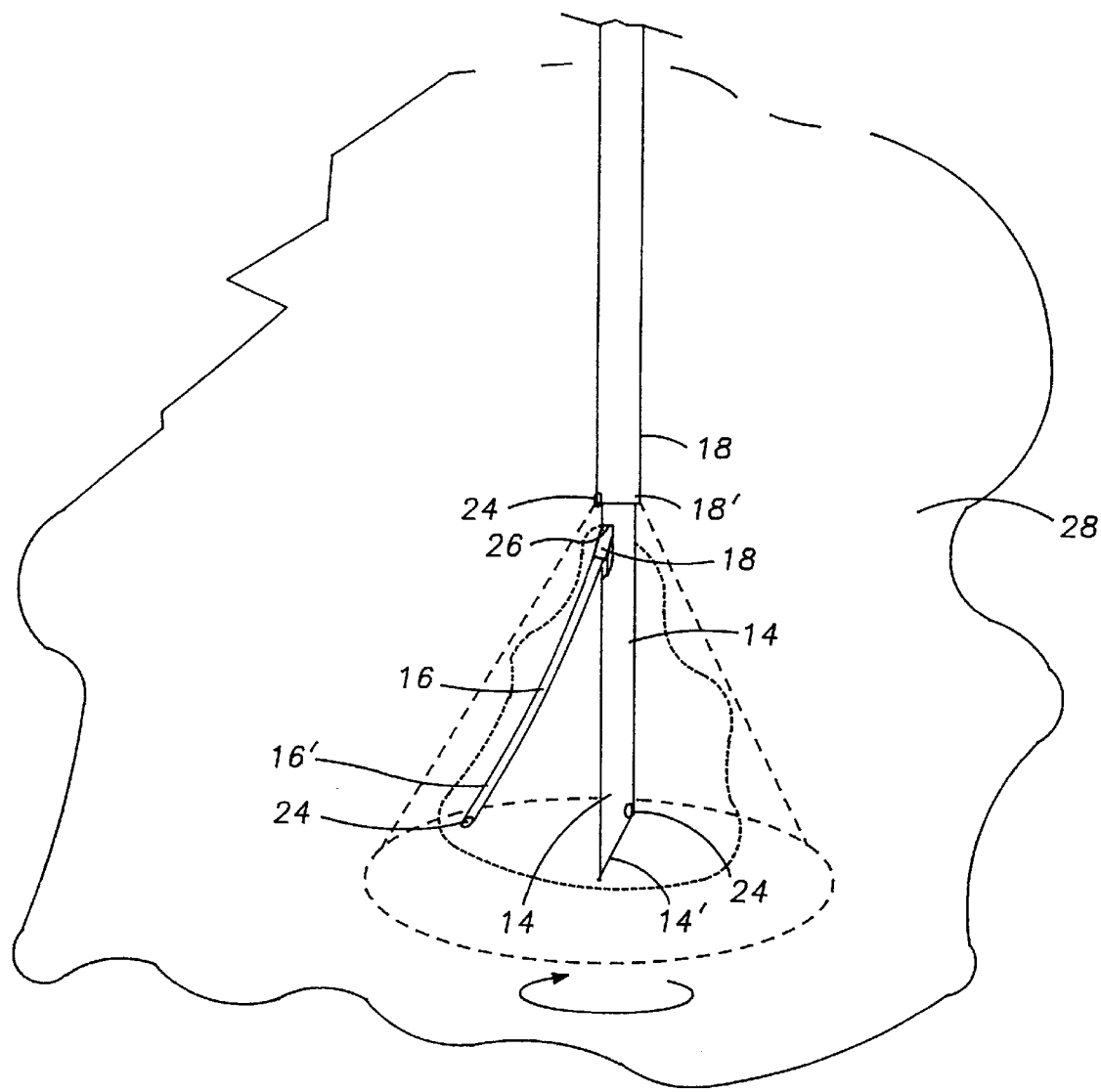
FIG. 2 is a perspective view of a conic geometric ablation achieved with the apparatus of FIG. 1.

As illustrated in FIG. 2, primary antenna 14 has been introduced into a selected tissue mass 28. Subsequently, secondary antenna distal end 16' is advanced out of aperture 26 and into selected tissue mass 28. Insulation sleeves 18 are adjusted for primary and secondary antennas 14 and 16 respectively. RF, microwave, short wave and the like energy is delivery to antenna 16 in a monopolar mode (RF), or alternatively, multiple antenna device 12 can be operated in a bipolar mode (RF). Multi antenna device 12 can be switched between monopolar and bipolar operation and has multiplexing capability between antennas 14 and 16. Secondary antenna distal end 16' is retracted back into primary antenna 14, and primary antenna is then rotated. Secondary antenna distal end 16' is then introduced into selected tissue mass 28. Secondary antenna may be introduced a short distance into selected tissue mass 28 to ablate a small area. It can then be advanced further into any number of times to create more ablation zones. Again, secondary antenna distal end 16' is retracted back into primary antenna 14, and primary antenna 14 can be, (i) rotated again, (ii) moved along a longitudinal axis of selected tissue mass 28 to begin another series of ablations with secondary antenna distal end 16' being introduced and retracted in and out of primary antenna 14, or (iii) removed from selected tissue mass 28. A number of parameters permit ablation of selected tissue masses 28 of different sign and shapes including a series of ablations having primary and secondary antennas 14 and 16 with variable length ablation surfaces and the use of sensor 24.

Figure 3:
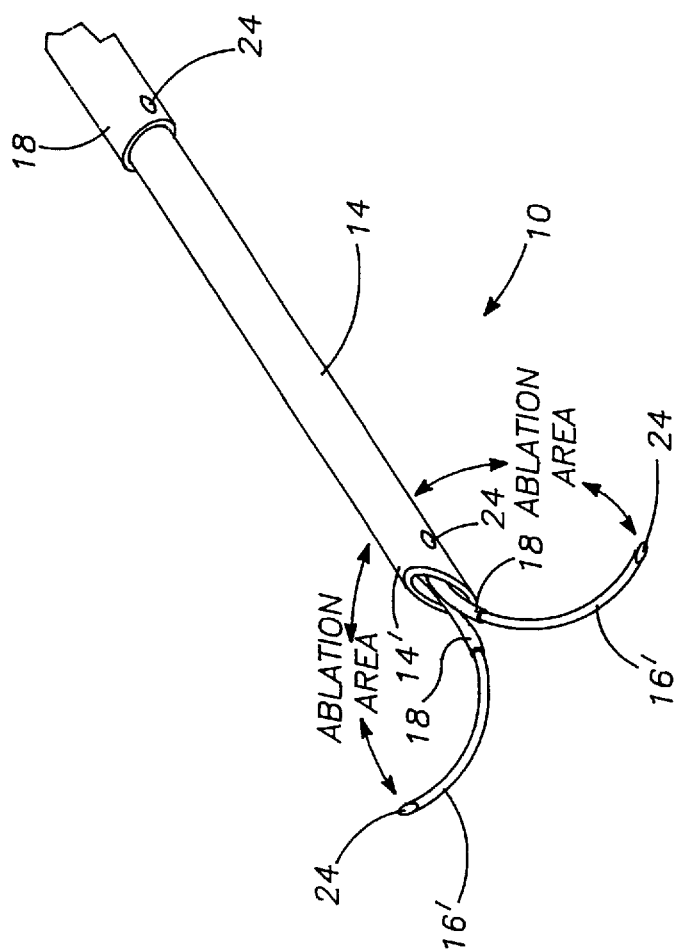
FIG. 3 perspective view of the multiple antenna ablation apparatus of the present invention with two secondary antennas.

In FIG. 3, two secondary antennas 16 are each deployed out of distal end 14' and introduced into selected tissue mass 28. Secondary antennas 16 form a plane and the area of ablation extends between the ablation surfaces of primary and secondary antennas 14 and 16. Primary antenna 14 can be introduced in an adjacent relationship to selected tissue mass 28. This particular deployment is particularly useful for small selected tissue masses 28, or where piercing selected tissue mass 28 is not desirable. Primary antenna 14 can be rotated, with secondary antennas 16 retracted into a central lumen of primary antenna 14, and another ablation volume defined between the two secondary antennas 16 is created. Further, primary electrode 14 can be withdrawn from its initial position adjacent to selected tissue mass 28, repositioned to another position adjacent to selected tissue mass 28, and secondary antennas 16 deployed to begin another ablation cycle. Any variety of different positionings may be utilized to create a desired ablation geometry for selected tissue mass of different geometries and sizes.

Figure 4:
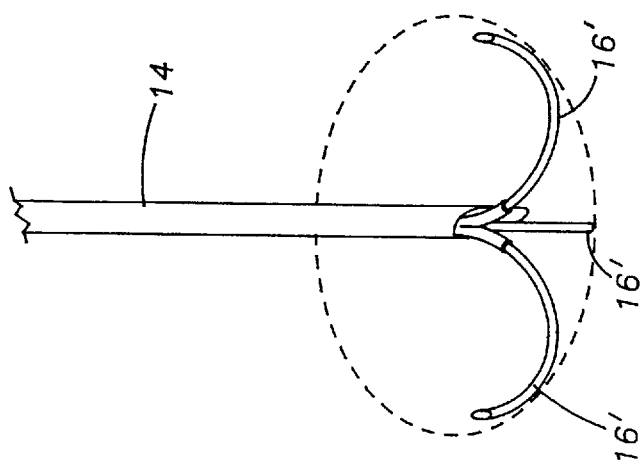
FIG. 4 is a perspective view illustrating the adjacent positioning of two secondary antennas next to a selected tissue mass.

In FIG. 4, three secondary antennas 16 are introduced into selected tissue mass 28. The effect is the creation of an ablation volume without leaving non-ablated areas between antenna ablation surfaces. The ablation is complete.

Figure 5:
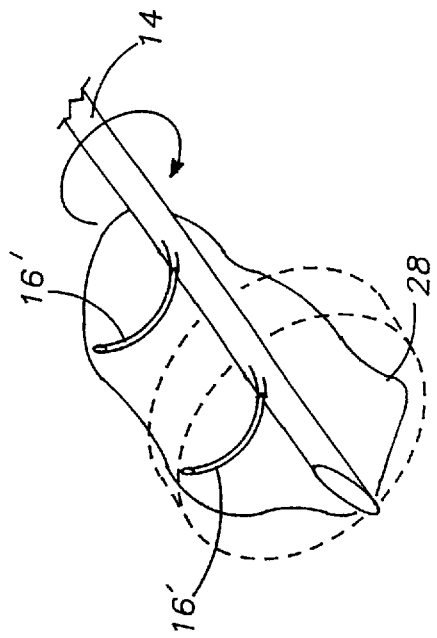
FIG. 5 is a perspective view illustrating the positioning of the multiple antenna ablation apparatus in the center of a selected tissue mass, and the creation of a cylindrical ablation.

Referring now to FIG. 5, a center of selected tissue mass 28 is pierced by primary antenna 14, secondary antennas 16 are laterally deployed and retracted, primary antenna 14 is rotated, secondary antennas 16 are deployed and retracted, and so on until a cylindrical ablation volume is achieved. Multiple antenna device 12 can be operated in the bipolar mode between the two secondary antennas 16, or between a secondary antenna 16 and primary antenna 14. Alternatively, multiple antenna device 12 can be operated in a monopolar mode.

Secondary antennas 16 can serve the additional function of anchoring multiple antenna device 12 in a selected mass, as illustrated in FIGS. 6(a) and 6(b). In FIG. 6(a) one or both secondary antennas 16 are used to anchor and position primary antenna 14. Further, one or both secondary antennas 16 are also used to ablate tissue. In FIG. 6(b), three secondary antennas are deployed and anchor primary antenna 14.

FIG. 6(c) illustrates the infusion capability of multiple antenna device 12. Three secondary antennas 16 are positioned in a central lumen 14" of primary antenna 14. One or more of the secondary antennas 16 can also include a central lumen coupled to an infusion source. Central lumen 14" is coupled to an infusion source and delivers a variety of infusion mediums to selected places both within and outside of the targeted ablation mass. Suitable infusion mediums include but are not limited to, therapeutic agents, conductivity enhancement mediums, contrast agents or dyes, and the like. An example of a therapeutic agent is a chemotherapeutic agent.

Figure 8:
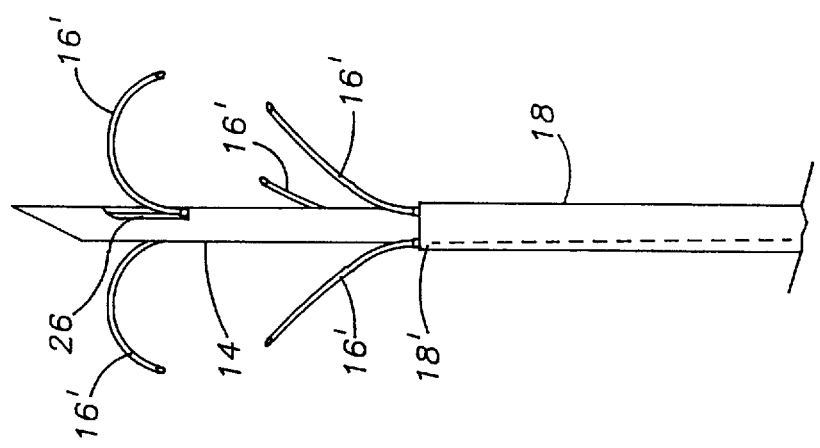
FIG. 8 is perspective view of the multiple antenna ablation of the present invention illustrating the deployment of two secondary antennas from the primary antenna, and the deployment of three secondary antennas from the distal end of the insulation sleeve surrounding the primary antenna.
Figure 7:
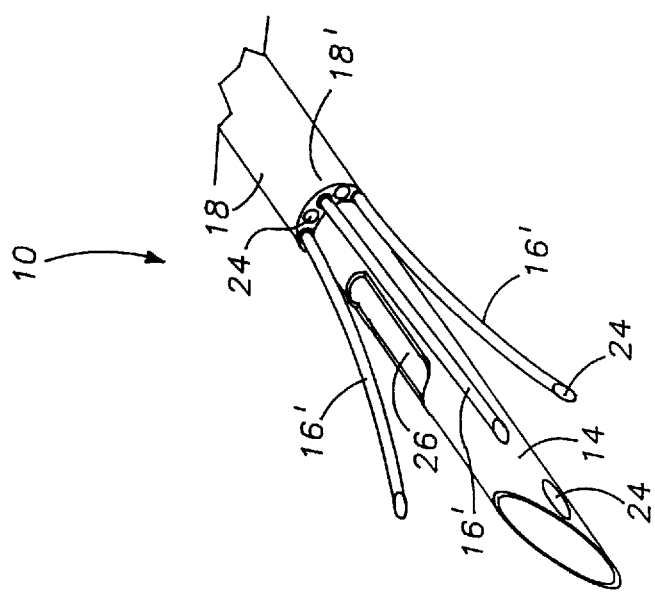
FIG. 7 is a perspective view of the multiple antenna ablation of the present invention illustrating the deployment of three secondary antennas from a distal end of the insulation sleeve surrounding the primary antenna.

As shown in FIG. 7 insulation sleeve 18 can include one or more lumens for receiving secondary antennas 16 which are deployed out of an insulation sleeve distal end 18'. FIG. 8 illustrates two secondary antennas 16 being introduced out of insulation sleeve distal end 18', and two secondary antennas 16 introduced through apertures 26 formed in primary antenna 14. As illustrated, the secondary electrodes introduced through apertures 26 provide an anchoring function. It will be appreciated that FIG. 8 illustrates how secondary antennas 16 can have a variety of different geometric configurations in multiple antenna device 12.

A feedback control system 29 is connected to energy source 20, sensors 24 and antennas 14 and 16. Feedback control system 29 receives temperature or impedance data from sensors 24 and the amount of electromagnetic energy received by antennas 14 and 16 is modified from an initial setting of ablation energy output, ablation time, temperature, and current density (the "Four Parameters"). Feedback control system 29 can automatically change any of the Four Parameters. Feedback control system 29 can detect impedance or temperature and change any of the Four Parameters. Feedback control system can include a multiplexer to multiplex different antennas, a temperature detection circuit that provides a control signal representative of temperature or impedance detected at one or more sensors 24. A microprocessor can be connected to the temperature control circuit.

The following discussion pertains particularly to the use of an RF energy source and RF multiple antenna device 12. It will be appreciated that devices similar to those associated with RF multiple antenna device 12 can be utilized with laser optical fibers, microwave devices and the like.

Figure 9:
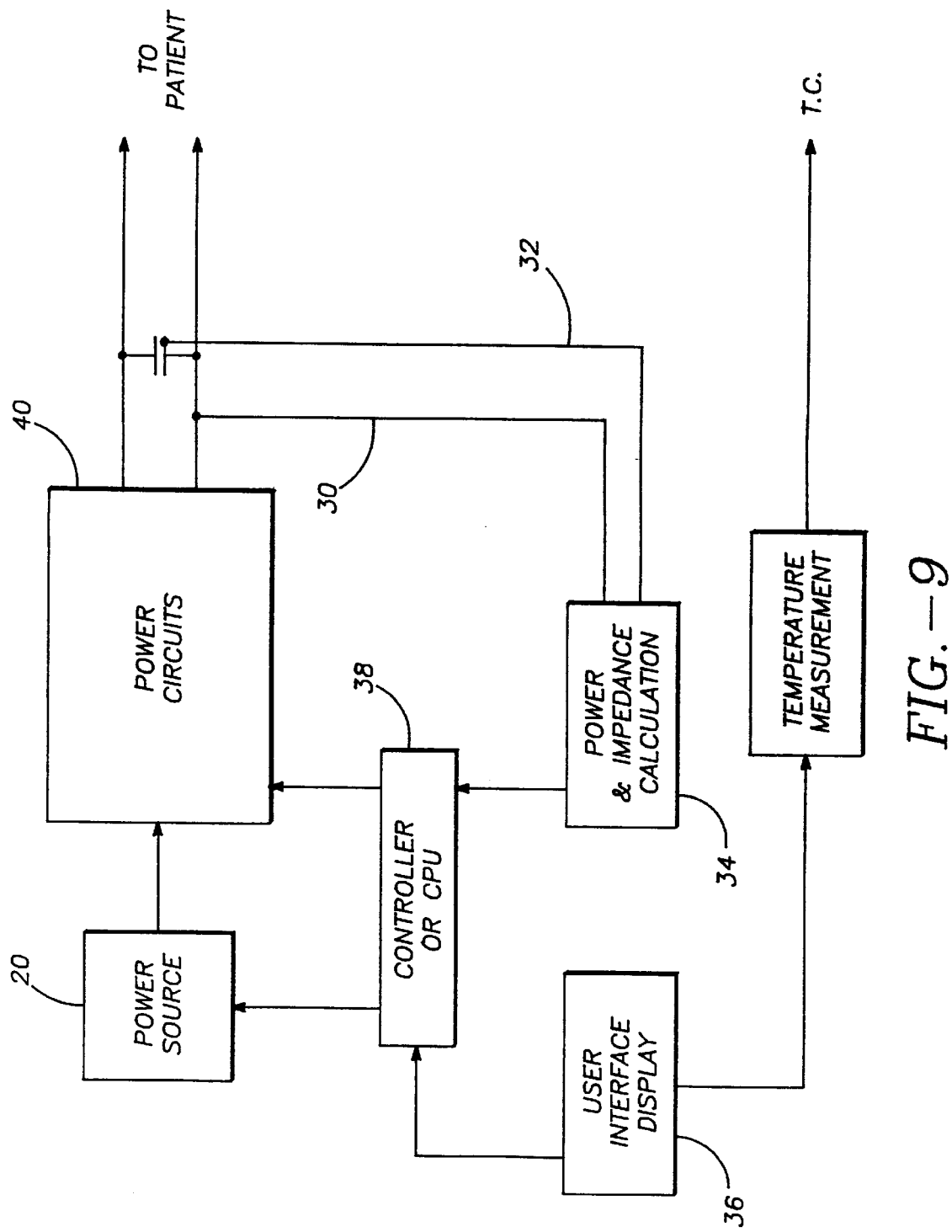
FIG. 9 is a block diagram illustrating the inclusion of a controller, energy source and other electronic components of the present invention.

Referring now to FIG. 9, all or portions of feedback control system 29 are illustrated. Current delivered through primary and secondary antennas 14 and 16 is measured by current sensor 30. Voltage is measured by voltage sensor 32. Impedance and power are then calculated at power and impedance calculation device 34. These values can then be displayed at user interface and display 36. Signals representative of power and impedance values are received by controller 38.

A control signal is generated by controller 38 that is proportional to the difference between an actual measured value, and a desired value. The control signal is used by power circuits 40 to adjust the power output in an appropriate amount in order to maintain the desired power delivered at the respective primary and/or secondary antennas 14 and 16.

In a similar manner, temperatures detected at sensors 24 provide feedback for maintaining a selected power. The actual temperatures are measured at temperature measurement device 42, and the temperatures are displayed at user interface and display 36. A control signal is generated by controller 38 that is proportional to the difference between an actual measured temperature, and a desired temperature. The control signal is used by power circuits 40 to adjust the power output in an appropriate amount in order to maintain the desired temperature delivered at the respective sensor 24. A multiplexer can be included to measure current, voltage and temperature, at the numerous sensors 24, and energy is delivered between primary antenna 14 and secondary antennas 16.

Controller 38 can be a digital or analog controller, or a computer with software. When controller 38 is a computer it can include a CPU coupled through a system bus. On this system can be a keyboard, a disk drive, or other non-volatile memory systems, a display, and other peripherals, as are known in the art. Also coupled to the bus are a program memory and a data memory.

User interface and display 36 includes operator controls and a display. Controller 38 can be coupled to imaging systems, including but not limited to ultrasound, CT scanners, X-ray, MRI, mammographic X-ray and the like. Further, direct visualization and tactile imaging can be utilized.

The output of current sensor 30 and voltage sensor 32 is used by controller 38 to maintain a selected power level at primary and secondary antennas 14 and 16. The amount of RF energy delivered controls the amount of power. A profile of power delivered can be incorporated in controller 38, and a preset amount of energy to be delivered can also be profiled.

Circuitry, software and feedback to controller 38 result in process control, and the maintenance of the selected power, and are used to change, (i) the selected power, including RF, microwave, laser and the like, (ii) the duty cycle (on-off and wattage), (iii) bipolar or monopolar energy delivery and (iv) infusion medium delivery, including flow rate and pressure. These process variables are controlled and varied, while maintaining the desired delivery of power independent of changes in voltage or current, based on temperatures monitored at sensors 24.

Figure 10:
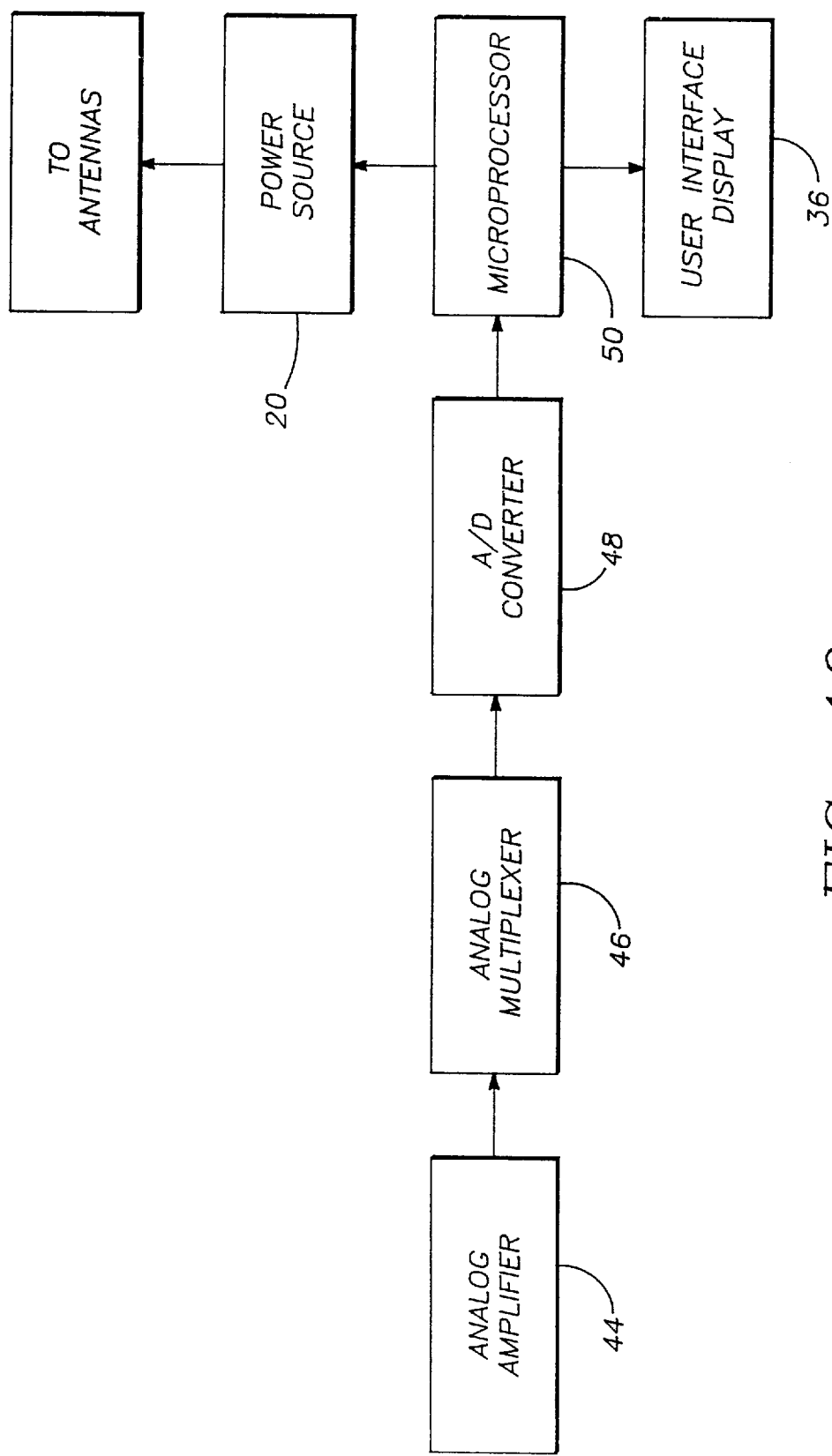
FIG. 10 is a block diagram illustrating an analog amplifier, analog multiplexer and microprocessor used with the present invention.

Referring now to FIG. 10, current sensor 30 and voltage sensor 32 are connected to the input of an analog amplifier 44. Analog amplifier 44 can be a conventional differential amplifier circuit for use with sensors 24. The output of analog amplifier 44 is sequentially connected by an analog multiplexer 46 to the input of A/D converter 48. The output of analog amplifier 44 is a voltage which represents the respective sensed temperatures. Digitized amplifier output voltages are supplied by A/D converter 48 to a microprocessor 50. Microprocessor 50 may be Model No. 68HCII available from Motorola. However, it will be appreciated that any suitable microprocessor or general purpose digital or analog computer can be used to calculate impedance or temperature.

Microprocessor 50 sequentially receives and stores digital representations of impedance and temperature. Each digital value received by microprocessor 50 corresponds to different temperatures and impedances.

Calculated power and impedance values can be indicated on user interface and display 36. Alternatively, or in addition to the numerical indication of power or impedance, calculated impedance and power values can be compared by microprocessor 50 with power and impedance limits. When the values exceed predetermined power or impedance values, a warning can be given on user interface and display 36, and additionally, the delivery of RF energy can be reduced, modified or interrupted. A control signal from microprocessor 50 can modify the power level supplied by energy source 20.

The foregoing description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

What is claimed is:

1. An ablation treatment apparatus, comprising:

a multiple antenna device configured to be coupled to an energy source, the multiple antenna device including a primary antenna with a lumen and a distal end sufficiently sharp to pierce tissue, and a first secondary antenna with a distal portion, the secondary antenna being at least partially positioned in the lumen as the primary antenna is introduced through tissue, at least a part of the distal portion is configured to be deployable from the lumen at a selected tissue site with at least one radius of curvature, wherein the first secondary antenna is electromagnetically coupled to the energy source; and at least one cable coupling the first secondary antenna to the energy source.

2. The apparatus of claim 1, wherein the primary antenna has an energy delivery surface with a length that is at least 20% of a length of an energy delivery surface of the first secondary antenna.

3. The apparatus of claim 1, wherein the primary antenna has an energy delivery surface with a length that is at least one-third of a length of an energy delivery surface of the first secondary antenna.

4. The apparatus of claim 1, wherein the primary antenna has an energy delivery surface with a length that is at least one-half of a length of an energy delivery surface of the first secondary antenna.

5. The apparatus of claim 1, further comprising:

a second secondary antenna including a distal portion with at least a part of the second secondary antenna distal portion configured to be deployed from the primary antenna with at least one radius of curvature, wherein each of the first and second secondary antennas have an energy delivery surface configured to create an ablation volume between the energy delivery surfaces of the first and second secondary antennas.

6. The apparatus of claim 5 further comprising:

a third secondary antenna including a distal portion with at least a part of the third secondary antenna distal portion configured to be deployed from the primary antenna with at least one radius of curvature, wherein each of the first, second and third antennas have an energy delivery surface configured to create an ablation volume between the energy delivery surfaces of the first, second and third antennas.

7. The apparatus of claim 1, further comprising:

an insulation sleeve positioned in a surrounding relationship around at least a portion of an exterior of the primary antenna.

8. The apparatus of claim 7, wherein the insulation sleeve is adjustably moveable along an exterior of the primary antenna.

9. The apparatus of claim 1, further comprising:

an insulation sleeve positioned in a surrounding relationship around at least a portion of an exterior of the first secondary antenna.

10. The apparatus of claim 9, wherein the insulation sleeve is adjustably moveable along an exterior of the first secondary antenna.

11. The apparatus of claim 1, further including a ground pad electrode with the primary and first secondary antennas operating in a monopolar mode.

12. The apparatus of claim 1, wherein the primary and first secondary antennas are RF antennas.

13. The apparatus of claim 12, wherein the apparatus is switchable between bipolar and monopolar operation.

14. The apparatus of claim 1, wherein the primary and first secondary antennas are microwave antennas.

15. The apparatus of claim 1, wherein the primary antenna is hollow and coupled to an infusion medium source to receive an infusion medium.

16. A method for creating an ablation volume in a selected tissue mass, comprising:

providing an energy source, an ablation device with a primary antenna, a first secondary antenna housed in a primary antenna lumen, the primary antenna including a distal end sufficiently sharp to pierce tissue and the first secondary antenna includes a distal portion with at least a part of the distal portion configured to be deployed from the lumen at a selected tissue site with at least one radius of curvature, wherein the first secondary antenna is electromagnetically coupled to the energy source;

inserting the primary antenna into the selected tissue mass with the first secondary antenna at least partially positioned in the primary antenna lumen;

advancing the distal portion of the first secondary antenna into the selected tissue from the primary antenna lumen;

delivering electromagnetic energy from a first secondary antenna energy delivery surface; and creating an ablation volume in the selected tissue site.

17. The method of claim 16, wherein the ablation device includes a second secondary antenna with a distal portion configured to be deployed from the lumen at a selected tissue site with at least a portion of the second secondary antenna distal portion having one radius of curvature and an energy delivery surface, and an ablation volume is created between the first and second secondary antennas ablation surfaces.

18. The method of claim 17, wherein the first and second secondary antennas are advanced out of the distal end of the primary antenna.

19. The method of claim 17, wherein the first and second secondary antennas are advanced out of separate ports formed in the primary antenna.

20. The method of claim 17, wherein the first and second secondary antennas are advanced from the primary antenna and define a plane.

21. The method of claim 17, wherein the ablation device includes a third secondary antenna with a distal portion configured to be deployed from the lumen at a selected tissue site with at least a portion of the distal portion having one radius of curvature and an energy delivery surface, and an ablation volume is created between the first, second and third secondary antennas energy delivery surfaces.

22. The method of claim 21, wherein the primary antenna has an energy delivery surface and an ablation volume is formed between the energy delivery surfaces of the first, second, and third secondary antennas and the energy delivery surface of the primary antenna.

23. The method of claim 22, wherein the ablation volume has a substantially spherical geometry.

24. The method of claim 22, wherein the primary antenna has an energy delivery surface length that is at least equal to 20% or more of a secondary antenna energy delivery surface length.

25. The method of claim 22, wherein the primary antenna has an energy delivery surface length that is at least equal to one-third or more of a secondary antenna energy delivery surface length.

26. The method of claim 22, wherein the primary antenna has energy delivery surface length that is at least equal to one-half or more of a secondary antenna energy delivery surface length.

27. The method of claim 16, wherein the primary and first secondary antennas are operated in a monopolar mode.

28. The method of claim 16, wherein the ablation device is operated in a bipolar mode.

29. A multi-modality apparatus, comprising:

an introducer including a lumen and a distal end sufficiently sharp to penetrate tissue; and an energy delivery device coupled to an energy source and at least partially positioned in the introducer as the introducer is advanced through tissue, the energy delivery device including a first electrode, a second electrode and a third electrode each having a tissue piercing distal portion, the first, second and third electrodes being at least partially positioned in the introducer as the introducer is advanced through tissue and deployable from the introducer to an expanded state of deployed first, second and third electrodes that distend laterally away from the introducer with a radius of curvature to form a shaped array of deployed electrodes at a tissue site, at least a portion of the shaped array of deployed electrodes surrounding at least a portion of the introducer when positioned at the selected tissue site, the first electrode including an infusion medium source port configured to deliver an infusion medium from the first electrode to the selected tissue site.

30. The apparatus of claim 29, further comprising:

a sensor positioned at a distal portion of the energy delivery device.

31. The apparatus of claim 30, further comprising:

a feedback control system coupled to the energy source and the sensor, wherein the feedback control system is responsive to a detected characteristic from the sensor and provides a delivery of ablation energy output from the energy source to the first energy delivery device.

32. The apparatus of claim 29, wherein a distal portion of the introducer is configured to be an introducer energy delivery device.

33. The apparatus of claim 29, further comprising:

a second energy delivery device at least partially positioned in the introducer as the introducer is advanced through tissue, the second energy delivery device including a distal portion configured to be deployable from the introducer at a selected tissue site, wherein at least a part of the second energy delivery device distal portion has at least one radius of curvature when deployed from the introducer.

34. The apparatus of claim 29, wherein the first energy delivery device is an RF electrode and the energy source is an RF source.

35. The apparatus of claim 29, wherein the first energy delivery device is a laser delivery device and the energy source is a laser.

36. The apparatus of claim 29, wherein the first energy delivery device is a microwave antenna and the energy source is a microwave source.

37. An ablation apparatus, comprising:

an introducer including a lumen and a distal end sufficiently sharp to penetrate tissue;

a first energy delivery device at least partially positioned in the introducer as the introducer is advanced through tissue, the first energy delivery device including a distal portion deployable from the introducer at a selected tissue site, wherein at least a part of the first energy delivery device distal portion has at least one radius of curvature when deployed from the introducer and the first energy delivery device is electromagnetically coupled to an energy source, the first energy delivery device including an infusion medium source port configured to deliver an infusion medium from the first energy delivery device to the selected tissue site;

a monitoring device at least partially positioned in the introducer as the introducer is advanced through tissue, the monitoring device including a distal portion deployable from the introducer at a selected tissue site; and a sensor positioned at the distal portion of the monitoring device.

38. The apparatus of claim 37, further comprising:

a feedback control system coupled to the energy source and the sensor, wherein the feedback control system is responsive to a detected characteristic from the sensor and provides a delivery of ablation energy output from the energy source to the first energy delivery device.

39. The apparatus of claim 37, wherein a distal portion of the introducer is configured to be an introducer energy delivery device.

40. The apparatus of claim 37, further comprising:

a second energy delivery device at least partially positioned in the introducer as the introducer is advanced through tissue, the second energy delivery device including a distal portion configured to be deployable from the introducer at a selected tissue site, wherein at least a part of the second energy delivery device distal portion has at least one radius of curvature when deployed from the introducer.

41. The apparatus of claim 37, wherein the first energy delivery device is an RF electrode and the energy source is an RF source.

42. The apparatus of claim 37, wherein the first energy delivery device is a laser delivery device and the energy source is a laser.

43. The apparatus of claim 37, wherein the first energy delivery device is a microwave antenna and the energy source is a microwave source.

* * * * *